United States Patent [19]
Tham et al.

[11] Patent Number: 5,912,656
[45] Date of Patent: Jun. 15, 1999

[54] DEVICE FOR PRODUCING A DISPLAY FROM MONITORED DATA

[75] Inventors: Robert Q. Tham, Middleton; Howard E. Mars, Jr., Verona, both of Wis.

[73] Assignee: Ohmeda Inc., Liberty Corner, N.J.

[21] Appl. No.: 08/270,208

[22] Filed: Jul. 1, 1994

[51] Int. Cl.[6] .................................................. G09G 5/00
[52] U.S. Cl. ........................ 345/112; 345/150; 600/300
[58] Field of Search .................................. 345/112, 113, 345/114, 150, 133; 128/709, 710, 712

[56] References Cited

U.S. PATENT DOCUMENTS

| | | | |
|---|---|---|---|
| 3,924,231 | 12/1975 | McClure | 340/366 |
| 3,961,306 | 6/1976 | Anstey | 340/15.5 |
| 3,978,470 | 8/1976 | McGuire | 340/324 |
| 4,051,522 | 9/1977 | Healy et al. | 128/903 |
| 4,576,178 | 3/1986 | Johnson | 128/670 |
| 4,771,274 | 9/1988 | Havel | 340/703 |
| 4,857,905 | 8/1989 | Ogawa | 345/113 |
| 5,140,519 | 8/1992 | Friesdorf et al. | 364/413.03 |
| 5,241,473 | 8/1993 | Ishihara et al. | 348/163 |
| 5,254,979 | 10/1993 | Trevett et al. | 345/113 |
| 5,262,944 | 11/1993 | Weisner et al. | 128/712 |
| 5,351,067 | 9/1994 | Lumelsky et al. | 345/113 |
| 5,447,164 | 9/1995 | Shaya et al. | 128/710 |
| 5,540,232 | 7/1996 | Laney et al. | 600/510 |

FOREIGN PATENT DOCUMENTS 2 009 934 7/1978 United Kingdom.
2 009 934 6/1979 United Kingdom.

OTHER PUBLICATIONS

Murch, Jerry and Huber, John, *Colour–the logical step*, 8181 New Electronics, vol. 15, Jun. 1982, No. 12, London, Great Britain.

Hillmer, K. and Muller, M., *PAN–2 Colour Display System*, 8011 Brown Boveri Review, vol. 66, Oct. 1979, No. 10.

March et al —*New Electronics Incorporating Electronics Today*, vol. 15, No. 12, Jun. 1982, pp. 28–32.

Hillmer et al —*Brown Boveri Review*, vol. 66, No. 10, Oct. 1979, pp. 662–667.

*Primary Examiner*—Matthew Luu
*Attorney, Agent, or Firm*—Whyte Hirschboeck Dudek SC

[57] ABSTRACT

The device for producing a display from monitored data functions to read, store, encode, and integrate monitored data of at least one data type from at least one monitoring device so that the related or unrelated datum is comprehensible at a glance by a user. Encoding data of a particular data type produces a color indicia and a graphic indicia that are the basic integration components. Integrating indicia of at least one data type produces a single superimposed and/or multidimensional image capable of portraying a present and historical data combination reflecting the monitored data's relative value at some point in time.

39 Claims, 6 Drawing Sheets

DEVICE FOR PRODUCING A DISPLAY FROM MONITORED DATA

FIELD OF THE INVENTION

This invention relates to a device that produces a display, and in particular, to a device that reads, stores, encodes, and integrates monitored data from at least one monitoring apparatus into color and/or graphic multidimensional images that are comprehensible at a glance by a user.

PROBLEM

It is a problem in the field of devices that produce displays for medical monitoring devices, to display the present and/or historic values of monitored data on a common data display device in a manner that facilitates comprehension at a glance. Among the ways comprehension at a glance is inhibited include displaying information in either a complex format, an illogical format, or a format demanding focused attention on individually displayed datum. In each case, critical information is not readily comprehensible at a glance. A display may be further complicated by attempting to simultaneously represent present and historic values for monitored data of one or more data types.

Inadequacies among conventional devices that produce monitored data displays include but are not limited to the following examples. One approach is to visually represent audio input with colored lights or Light Emitting Diodes (LEDs) which correspond to variations in the audio input's frequency, volume, or frequency of occurrence. This approach provides a present value display for monitored data but is limited in flexibility due to a fixed lighting arrangement and that it does not display a monitored data history. In addition, color combinations create complex and often cryptic displays that limit the practical number of readily comprehensible combinations.

Another approach is to use audible representations of monitored data where predetermined tones are varied in their tone frequency, volume, or frequency of occurrence. This approach, however, fails to provide a monitored data history and it often requires users to distinguish between similar tones. Audible representations also limit the practical number of simultaneous sounds since overlapping tones or tone pulses require users to sort a symphony of competing sounds.

Another common arrangement is the fixed field screen display which subdivides a display screen into independent fields or regions each dedicated to displaying information related to a single monitored data type. While this approach displays multiple data types simultaneously, a user must view and interpret information from independent screen subdivisions before the aggregate of displayed information is comprehensible.

The approaches described above do not adequately provide present value and/or historic value perspectives in color, graphic, and/or multidimensional displays. In addition, the devices producing the above described displays fail to provide an integrated display for monitored data from multiple monitoring devices that is comprehensible at a glance, which is important in the professional and home medical monitoring apparatus field.

SOLUTION

The present invention solves the above described problems and achieves a technical advance in the field of devices producing monitored data displays for at least one monitoring apparatus. Ideally, a display integrates monitored data into a present and/or historical value display form that is readily comprehensible at a glance. To facilitate comprehension at a glance, the present invention encodes and integrates monitored data from at least one monitoring apparatus into color and/or graphic displays that visually portray the present and/or historic values for each of a plurality of monitored data types.

In practice, at least one of a plurality of monitoring apparatus attached to the device of the present invention, is configured to monitor data of a predetermined type and to make the monitored data available in analog or digital form. The device of the present invention reads the monitored data made available by each monitoring apparatus, typically by a periodic sampling of present values. Each present value can be encoded for immediate display, and/or simultaneously stored as a series of uninterpreted stored values in a data storage device or area separate from each monitoring apparatus. The reading and storing of monitored data is performed for each monitored data type whether the data is provided by one monitoring apparatus or multiple independent monitoring apparatus. Once stored, the series of present values provides the basis for a present value history for each monitored data type.

To produce a display readily comprehensible at a glance, each stored value is retrieved and encoded to correspond to a representative color indicia and/or a graphic indicia which are the basic elements that are subsequently integrated and projected by a display device. A color indicia includes, but is not limited to any hue, shade, fade, color spectrum, color continuum, or any combination thereof that is supported by an accompanying display device. A graphic indicia includes, but is not limited to any geometric, multidimensional, alphanumeric, graphic icon, or other character combination capable of being displayed by an accompanying display device. Indicia from encoded present values are integrated into various superimposed and/or multidimensional combinations suitable for projection by a display device. For example, integrating the color indicia and graphic indicia of a monitored datum's present value provides the basis for representing the present value as a colored integer. Similarly, integrating the indicia from a series of present values provides the basis for a multidimensional history representing present and past values of one or many types of monitored data where each indicia is updated independently.

While the present invention is useful in the medical monitoring field, it is also applicable in any field where monitored data is represented on a display device. Examples of these applications include, but are not limited to, automotive, aerospace, communications, manufacturing, mechanical, power and chemical plants, environmental systems, security systems, and transportation.

DETAILED DESCRIPTION

Background and Hardware Architecture

Figure 1:
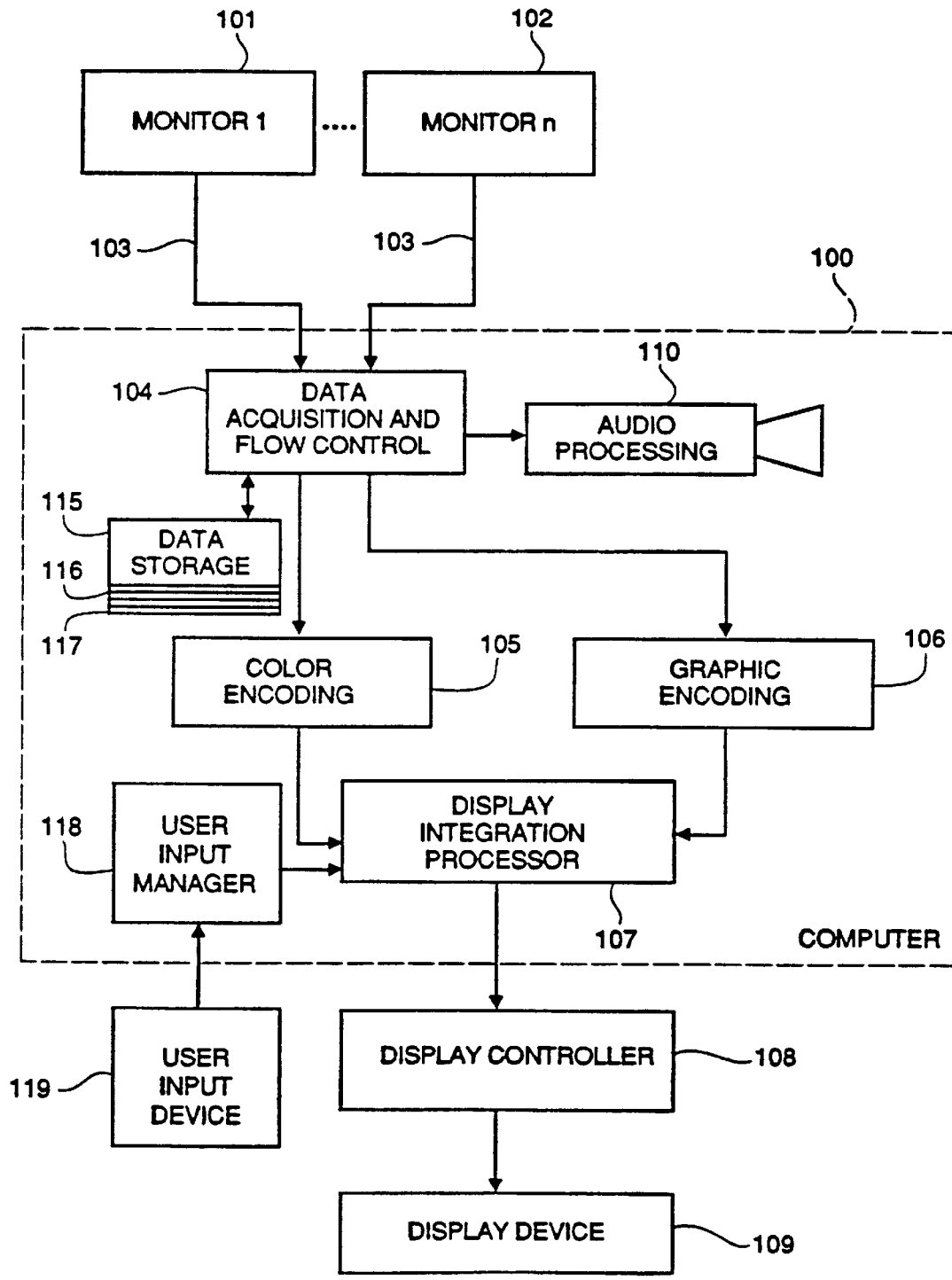
FIG. 1 illustrates a hardware configuration in block diagram form.

FIG. 1 illustrates the hardware architecture of the device 100 in block diagram form, in addition to an accompanying plurality of monitors 101 through 102, at least one user input device 119, and at least one display device 109. The plurality of monitors 101 through 102 are configured to monitor data of a predetermined type and to make the monitored data available in analog or digital form. Whether any one of the monitors 101 through 102 are configured to monitor a single data type or multiple independent data types concurrently, the most recently available monitored datum of any one data type is a present value. Therefore, a data type's present value may be updated at any time, typically by obtaining a new sample, depending on the scheme the monitor 101 through 102, or the data acquisition and flow control device 104, may follow. A former present value is called a historic value. A series of present values for a given data type is typically held in storage and defines a present value history where there is only one most recent present value, and any remaining values are historic, that is, they form a history.

The data acquisition and flow control device 104 is connected either directly or indirectly to each of the plurality of monitors 101 through 102 via communication connectors 103. The communication connectors 103 can be any standard or proprietary data communication interface. The device 104 reads or otherwise acquires monitored data from any or all of the plurality of monitors 101 through 102 on a schedule that may include, but is not limited to, any combination of regular, irregular, or event driven time intervals, in any manner that is ordered or unordered, synchronized or unsynchronized, parallel or seriatim, or any combination thereof.

Once read or otherwise acquired, the monitored data is stored in a data storage area or device 115 in one of a plurality of data files 116 through 117, as uninterpreted datum representing the most recent present value for a particular data type. Each data file 116 through 117 corresponds to a monitored data type from a specific monitor 101 through 102, and contains a present value series for each monitored data type. The data storage area 115 may be a common or distributed computer memory including, but not limited to, a semi-conductor type memory, but may also be an independent storage device, a plurality of distributed storage devices, or any combination thereof, each being directly or indirectly accessible to the data acquisition and flow control device 104, and containing storage media including, but not limited to, disk and tape.

The data acquisition and flow control device 104 also distributes monitored data for subsequent processing by color encoding 105 and/or graphic encoding 106. For a recently read present value, the device 104 can simultaneously store and distribute the present value for subsequent encoding, or store and distribute the present value in combination with a present value series retrieved from the data storage area 115. Similarly, the device 104 can store a recently read present value and subsequently retrieve a complete present value series that includes the recently read present value so that the complete present value series can be distributed for subsequent processing by color and/or graphic encoding 105 and 106 as a unit. The specific data and data file from which a present value series is retrieved is either preprogrammed or subject to a user request. In either case, a representative color indicia and/or graphic indicia is then produced by the respective encoders 105 or 106 for each present value retrieved.

A color indicia includes, but is not limited to a hue, shade, fade, color spectrum, color continuum, or any combination thereof that is supported by an accompanying display device. A graphic indicia includes, but is not limited to any geometric, multidimensional, alphanumeric, graphic icon, or other character combination capable of being displayed by an accompanying display device. The following definitions are also useful to further define the term color indicia, which may be used synonymously with the word color.

A hue is a distinguishable color typically including, but not limited to, blue, green, yellow, red, or any combination thereof. A shade is any selected gradation of any one hue, where the gradations range in the black to white spectrum so that moving toward the black end of the spectrum produces a darker version of the hue, and moving toward the white end of the spectrum produces a lighter version of the hue. Fade or fading is where a hue is incrementally diluted in its intensity or clarity, toward becoming indistinguishable from a predefined background color that is typically, but not necessarily, neutral. A color spectrum is the complete and continuous range of hues and shades therebetween. A color continuum is a group of simultaneously displayed hues and/or shades where the display can be a traditional color spectrum, or a random spectrum that may vary, repeat, and/or skip a hue or shade gradation for any reason.

The display integration processor 107 integrates the encoded indicia from encoders 105 and 106 into various superimposed and/or multidimensional combinations as discussed herein and illustrated in FIGS. 2 through 10. The processor 107 is based on standard computer processor hardware. Each integrated indicia combination is subsequently projected by a display device 109 via display controller 108. The display device 109 may be a traditional Cathode Ray Tube, flat plasma or other projection screen, or any device capable of displaying holographic or virtual images in space or in a visor or hood. The displays produced by the device 100 are not dependent on any specific type display controller 108 or display device 109, and may exist in conjunction with any processed audio 110 and/or sensory signal produced or delivered via display device 109.

The user input manager 118 is responsive to user commands delivered to device 100 through a user input device 119. The user input device 119 may be any device that accepts input by any means including but not limited to, voice instruction, direct or indirect pointing at a portion of a display screen, or keyboard commands.

Integrated Present Value Example

Figure 2:
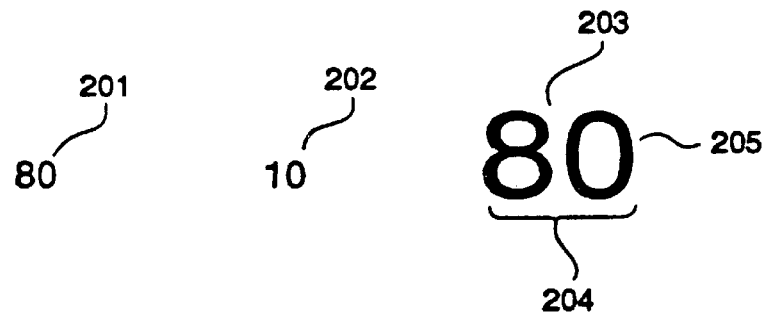
FIG. 2 illustrates the indicia from two monitored data types integrated into a color on graphic image.

Integrating a present value's indicia produces numerous displays ranging from one indicia representing one present value, to multiple indicia each representing the same present value or a plurality of present values. FIG. 2 illustrates two indicia corresponding to two separate present values. The figure illustrates a first present value 201 and a second present value 202 prior to encoding and integration, and the same two present values after encoding and integration 203.

In 203, the first present value's encoded indicia is a numeric graphic 204 and the second present value's encoded indicia is a color 205 that is superimposed onto the numeric graphic 204. The integration result is a single image 203 representing hero present values which are capable of being comprehended at a glance. When the second present value 202 represented by color indicia 205, changes value, a new color corresponding to the new present value is superimposed onto the underlying numeric graphic indicia 204. Similarly, the numeric graphic indicia 204 can change independent from the superimposed color indicia 205. The FIG. 2 example illustrates only the most recent present values without displaying a history.

Alternatively, the integrated image 203 can represent one present value in two indicia forms. For example, the first present value 201 could be encoded as a color indicia 205 that is superimposed on its equivalent numeric graphic indicia 204.

Figure 3:
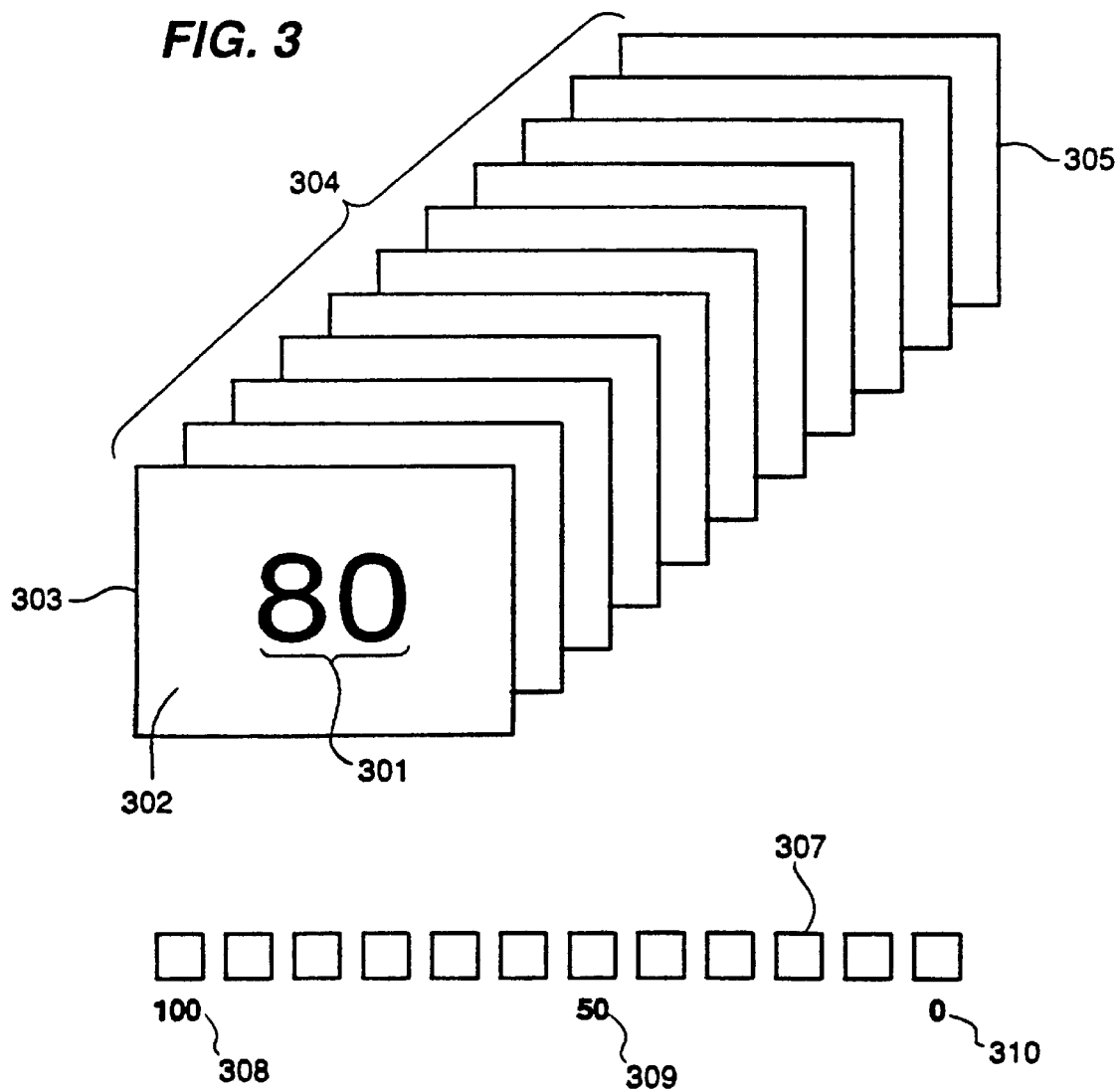
FIG. 3 illustrates two indicia from one monitored data type integrated into a multidimensional graphic on color image.

FIG. 3 illustrates another scenario where two indicia represent the same present value. Here, a numeric graphic indicia 301 is superimposed on a color indicia 302, where both indicia represent the same present value. One distinct advantage of having multiple indicia represent the same present value is that each indicia is highly recognize on its own so that when they are integrated, each indicia reinforces the other to facilitate an observers comprehension at a glance. Where an observer believes a first indicia represents a present value in a range of present values, the initial impression is instantly confirmed by the second indicia integrated with the first; the result being comprehension at a glance.

Integrated Present Value and Historic Value Example

FIG. 3 also illustrates a historic present value series represented by multiple overlapping cards 304 arranged from oldest value 305 to the most recent present value 303. The visible portions of the overlapping cards 304 represent former present values by displaying each card's color indicia. Only the most recent present value 303 is represented both by the color indicia 302 and graphic indicia 301. When a more recent present value of the same data type is available from one of the plurality of monitors 101 through 102, the more recent present value is encoded and integrated to replace the present value card 303. The present value card 303 would then be pushed back one position into the card series 304 so that only its color indicia is visible, and the oldest card 305 is no longer displayed in the series 304. Additionally, a user wishing to view the unobstructed numeric graphic indicia of a card in the card series 304, need only identify the desired card or cards by a user command via user input device 119. Identifying a card for recall is accomplished by any means including but not limited to voice instruction, direct or indirect pointing, or keyboard command. A recalled card may be displayed in any default area or a user defined area, and would appear in a form substantially the same as the present value card 303.

The operational range indicator 307 corresponds to at least one indicia concurrently on display. In FIG. 3, operational range indicator 307 corresponds to the color indicia in the present value card series 304, and indicates the relative range of potential present values that may be represented by the color indicia. Typically, the color indicia in an operational range is shaded. Numeric values 308, 309, and 310 assist in quantifying the relative range of potential present values. Numerically quantifying the operational range is useful where the range is portrayed by shaded color indicia.

Figure 4:
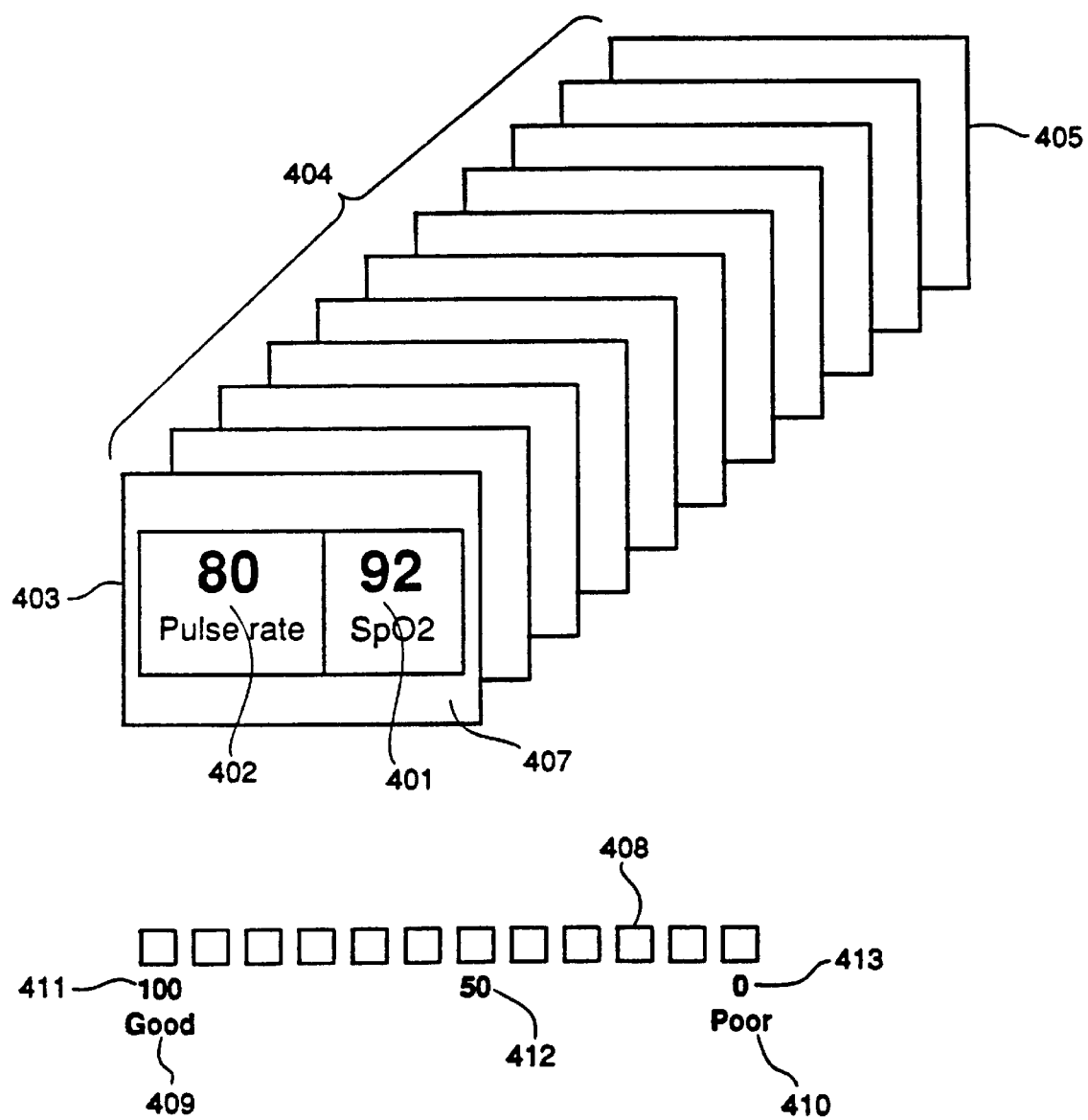
FIG. 4 illustrates multiple indicia from multiple monitored data types integrated into a multidimensional graphic on color image.

FIG. 4 illustrates a historic present value series represented as a card series 404 arranged from the oldest present value card 405 to the most recent present value card 403. Each card, however, contains indicia representing three present values: a first indicia 401 in numeric graphic form with alphabetic subtitle; a second indicia 402 in numeric graphic form with alphabetic subtitle; and a third indicia 407 in color form derived from combining present values 401 and 402, to illustrate the combined monitored measurement state for the most recent present value card 403. In a medical application, the FIG. 4 example is useful for displaying related data such as pulse rate 402, blood oxygen saturation 401, and the resulting blood color approximation 407. Using biologically correct colors or standardized colors is not mandatory. As with FIG. 3, individual cards from the card series 404 can be recalled by identifying the desired card or cards. The recalled card would appear in a form substantially the same as present value card 403. The operational range indicator 408 displays a range marked by relative terms "good" 409 and "poor" 410 in addition to the numeric references 411, 412, and 413, which provide additional meaning to each color or number along the range indicator.

Figure 5:
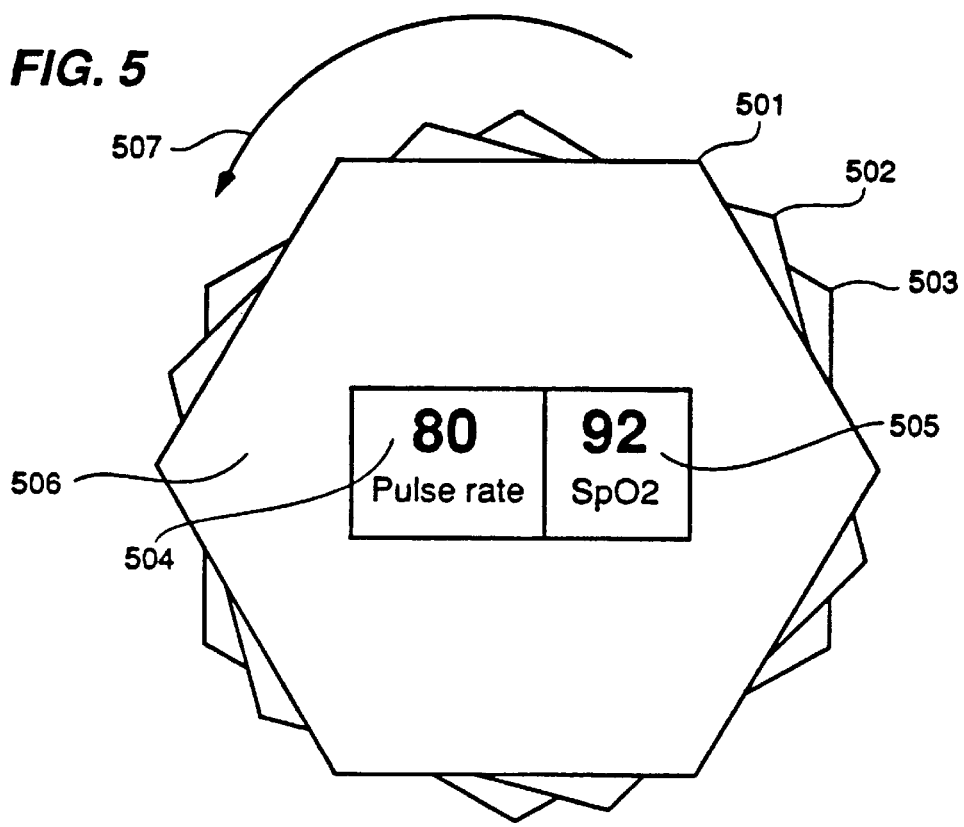
FIG. 5 illustrates multiple indicia from multiple monitored data types integrated into a rotating polygon with graphic on color indicia.

FIG. 5 illustrates a historic value display in the form of a polygon card series. Here, the top polygon 501 rotates as a function of time or a predetermined event's occurrence 507 while polygon shadows remain behind to display former present values as background color indicia 502 and 503. The partially obscured polygon 503 is the oldest display, followed by the next oldest 502 and the present value polygon 501. Similar to FIG. 4, FIG. 5 uses different indicia to represent three present values: a first indicia 504 in numeric graphic form with alphabetic subtitle; a second indicia 505 in numeric graphic form with alphabetic subtitle; and a third indicia 506 in color form derived from combining present values 504 and 505 to illustrate the combined monitored measurement state. In addition, the inner graphic form containing or highlighting the first indicia 504 and second indicia 505, can, but is not required to, vary in size, shape, and/or color, to correspond to the indicia therein.

Alternatively, the time elapsed since the last update for present value indicia 504, 505, and 506 can be displayed by fading each respective indicia as the polygon rotation 507 continues to mark time. The more faded the color indicia, the older the present value. The rotational direction and number of polygon edges, however, is application specific. The rotational direction, number of polygon edges, equality of polygon edges or angles, and consistency of polygon size, however, are application specific. For this reason, the present value polygon itself can, but is not required to, vary in size and/or shape in a uniform or a non-uniform fashion corresponding to the present value being represented.

Figure 6:
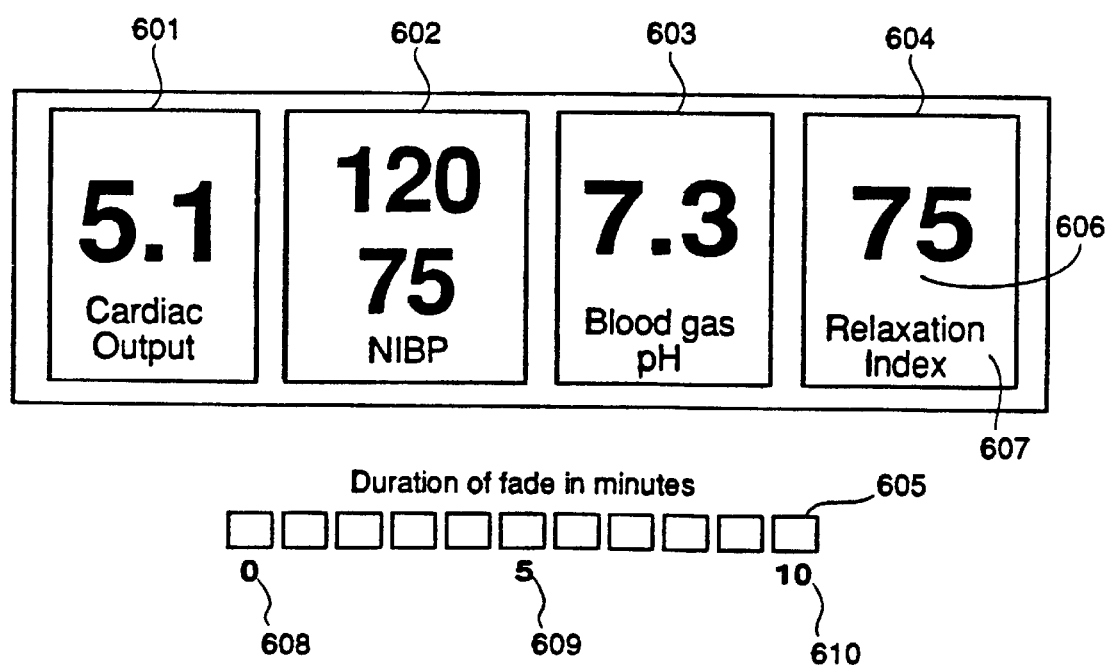
FIG. 6 illustrates multiple indicia from multiple monitored data types integrated into individual graphic on color images.

FIG. 6 illustrates multiple present values 601, 602, 603, and 604, each representing different monitored data types. Each present value is represented by a numeric graphic indicia 606 with alphabetic subtitle, superimposed on an equivalent color indicia 607 which fades over time as seen in present value example 604. Because each color indicia can be a different hue, the degree of fading relative to a time increment is displayed by the operational range indicator 605. The operational range indicator 605 corresponds to a single present value indicia, however, the range indicator 605 can also be selectably displayed for any one present value indicia, or a set of operational range indicators can be displayed simultaneously for each present value. Similarly, related data types can be displayed simultaneously where each data type is represented by a different shade. The numeric values 608, 609, and 610 indicate a time increment, here, in minutes.

Figure 7:
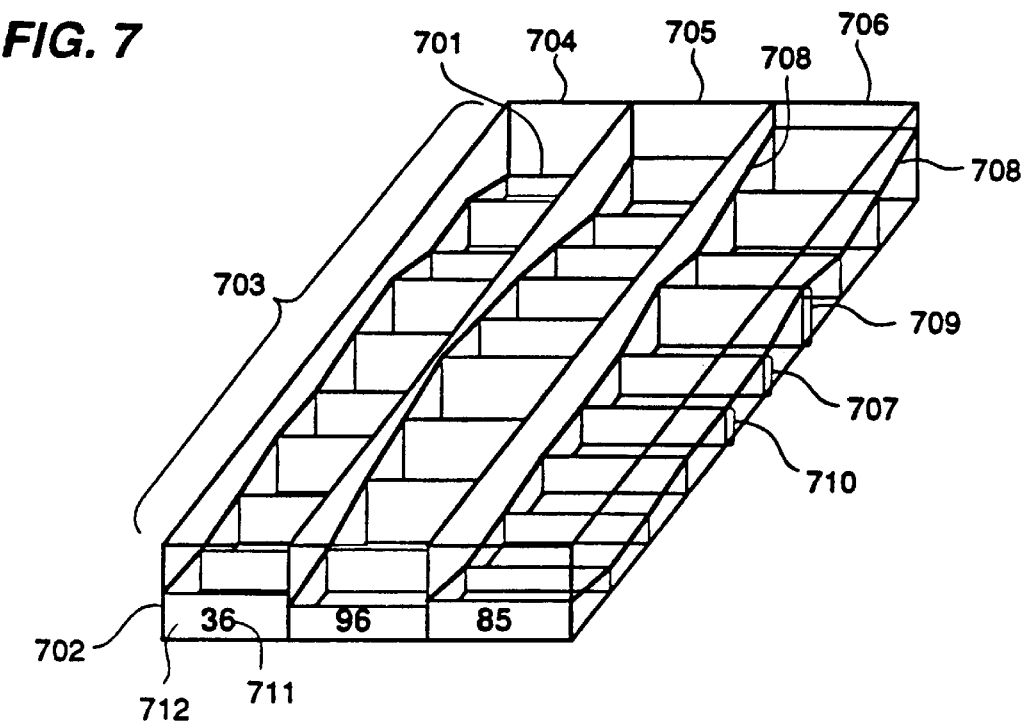
FIG. 7 illustrates multiple indicia from multiple monitored data types integrated into a multidimensional color and graphic image.

FIG. 7 illustrates a multidimensional present value and historic value integration for multiple monitored data. Each monitored data type is displayed in an individual alley 704, 705, and 706 where each alley contains a present value card series similar to card series 703. The cards in card series 703 provide a historic perspective ordered from the oldest value card 701 to the most recent present value card 702, and only the most recent present value card in card position 702 displays a numeric graphic indicia 711 superimposed on its equivalent color indicia 712. Subsequent cards in the card series 703, are retrievable by user command, as previously described, in order to display the numeric graphic indicia as seen on the present value card 702.

Further, each card in an alley can, but is not required, to occur with the same regularity as adjacent cards in an adjacent alley. Finally, any one card in a card series 703, as illustrated in alley 706, may vary in height 707 according to its value relative to the preceding and succeeding neighbor cards 709 and 710. For example, card 707 may vary in height from the preceding card 709 and succeeding card 710, and the height variation among the cards 707, 709, and 710 is highlighted by a conforming wave form 708 which provides a readily comprehensible summary at a glance.

Figure 8:
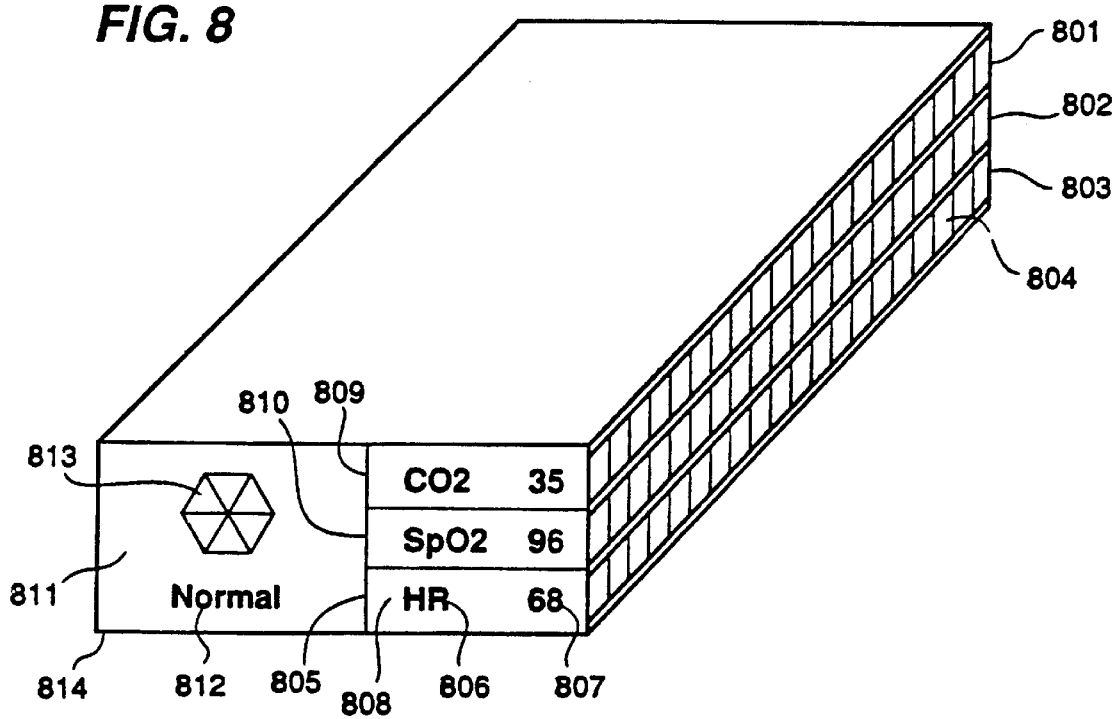
FIGS. 8 and 9 illustrate multiple indicia from multiple monitored data types integrated into a multidimensional color and graphic image with a historic color perspective.

FIG. 8 illustrates another present value and historic value integration for multiple monitored data. Here, the present value series for each monitored data type is displayed as a segmented color continuum 801, 802, and 803, where each segment in the continuum represents a present value in color indicia form. The segment in the segmented color continuum 803 for example, provide a historic perspective ordered from the oldest segment 804 to the most recent present value segment 805, and only the most recent present value segment 805 displays a numeric graphic indicia 807 with accompanying alphanumeric title 806 superimposed on an equivalent color indicia 808. Individual segments in the segmented color continuum 803 are retrievable by user command, as previously described, in order to display the numeric graphic indicia in a form substantially the same as seen on the present value segment 805. Further, each card segment in continuum 803 can, but is not required, to occur with the same regularity as segments in adjacent continuum 802 and 801. A derived measurement area 814 indicates the aggregate relationship between the most recent present values represented in areas 805, 809, and 810 respectfully. The derived measurement in area 814 is displayed by color indicia 811 and graphic indicia 813. The graphic indicia 813 can, but is not required to, represent the derived measurement as illustrated by the polygon embodiment of FIG. 5. In addition, the color indicia 811 selected to represent the derived measurement in area 814 may indicate relative states such as green for normal or good, yellow for warning, and red for bad. Here, the color indicia 811 indicates a normal condition as alphabetically represented by the word 812.

Figure 9:
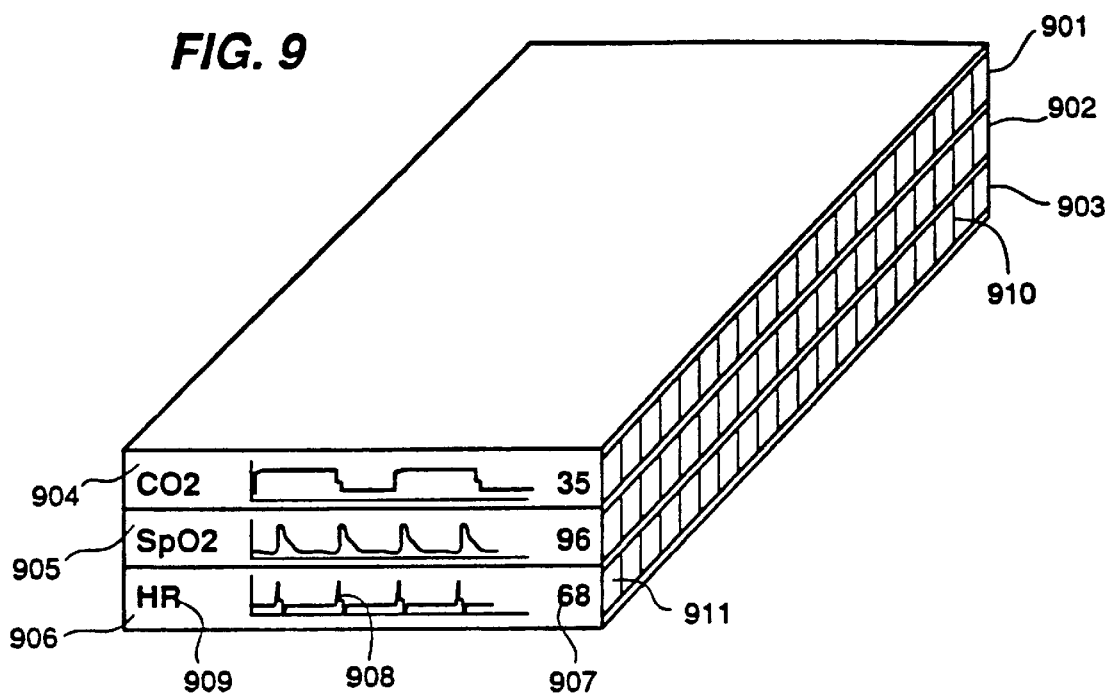

FIG. 9 is similar to FIG. 8 in that a present value series for each monitored data type displayed as a segmented color continuum 901, 902, and 903 respectfully. Each segment in the continuum represents a present value in color indicia form from oldest 910 to most recent 911. In addition, the corresponding color indicia 904, 905, and 906 each represents the most recent present value for each monitored data type. The most recent present value 911, for example, is also displayed as a numeric graphic indicia 907 with accompanying alphanumeric title 909, superimposed onto an equivalent color graphic indicia 906. The wave form graphic indicia 908 displays a present value history equivalent to at least the most recent portion of the corresponding segmented color continuum 903 along the side of the image.

Figure 10:
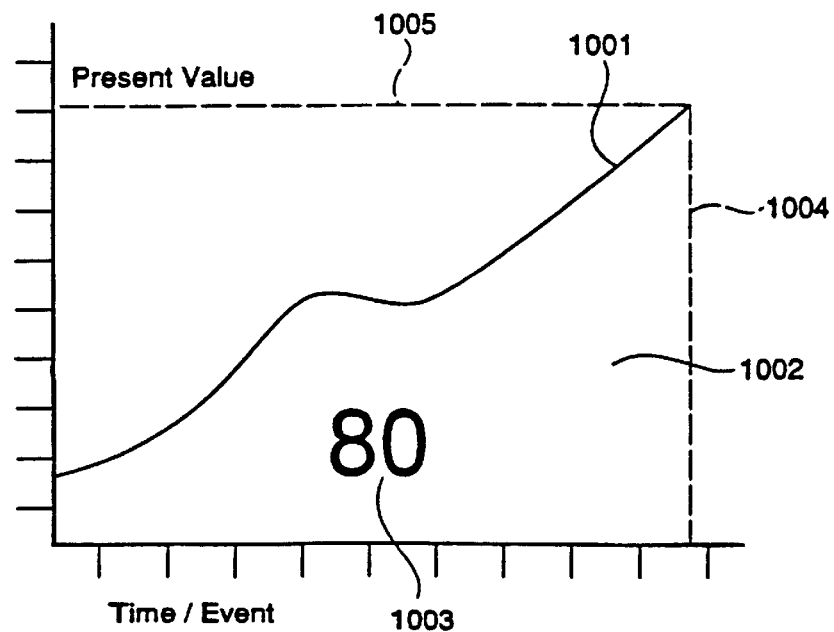
FIG. 10 illustrates three indicia representing one monitored data type integrated into a graphic and color image.

FIG. 10 illustrates a simple two dimensional integration involving three indicia from the same monitored data type.

Here a wave form graphic indicia 1001 floats on the equivalent color indicia 1002, and the equivalent numeric graphic indicia 1003 is superimposed on the coior indicia 1002. Indicators 1004 and 1005 highlight the most recent present value's coordinates on the present value axis and time/event axis. The time/event axis represents either regular time intervals or the occurrence of a predetermined event. Together, the integrated indicia provides a present and historical perspective that includes the most recent present value for a given monitored data type. A bar graph display is another variation on the FIG. 10 illustration.

Common Features of Integrated Indicia Display

FIGS. 3, 4, and 6 each display an operational range indicator 307, 408, and 605 respectively. Although the remaining Figures do not have an operational range indicator present, the absence does not preclude having the indicator for any type scenario involving integrated indicia.

The graphic form and/or size of any background graphic, foreground graphic, present value card, or operational range indicator illustrated in FIGS. 2–9, can, but are not required to, vary to correspond to the indicia therein. The shapes illustrated in the figures are for example only. For this reason, the graphic form implemented in practice may be a regular or irregular graphic form, or any combination of size, shape, and/or amplitude that may vary accordingly.

The colors used in any color indicia representing a present value may be randomly selected or have particular meaning. Colors having particular meaning may be as found in FIG. 7 where green represents good, yellow is moderate or a warning, and red is bad. Similarly, the color indicia may represent a commonly recognized color, including but not limited to, shades of oxygenated blood, for example, where red represents highly oxygenated blood and blue represents a low oxygen level.

Each FIG. 3 through 10 contains historic value cards or segments which may be recalled by user command input through a user input device 119 and interpreted by user input manager 118. Among the user commands used to recall a historic value include, but are not limited to, voice command, direct or indirect pointing at a portion of a display screen, and keyboard commands. A recalled historic value is then displayed in any default display area or a user defined display area, and would appear in a form substantially the same as the present value card fully visible in the front of a present value series.

Audio processor 110 interprets signals from the data acquisition and flow control device 104 to produce desired informational tones or tone pulses when a specific monitored data type is unavailable or otherwise unsuitable for display. One condition where data is unavailable for display is where communications fail between data acquisition and flow control device 104 and any one of the monitors 101 through 102. During a period of failed communications, any monitored data available for acquisition from any other monitor 101 through 102, continues to be acquired by the data acquisition and flow control device 104 as previously indicated. Due to the failed communications, display options include but are not limited to, sounding an audible warning for the user, providing a visual display for the user, providing a combination audio and visual indicator, processing the available monitored data around the missing data to provide an estimated display, or any combination thereof.

Data unsuitable for display includes, but is not limited to, data that was corrupted or otherwise contained anomalies prior to being acquired from a monitor 101 through 102, or data that was corrupted in the storage area 115 or from other internal processing by the device 100 of the present invention. In either situation, the monitored data is known to be incorrect or unreliable, and therefore may be displayed with an audible or visual warning, or not displayed at all.

Example of Use

One application of the present invention is a medical monitoring device for professional or home care monitoring applications. The displays cited as examples herein provide specific information at a glance where time does not permit studying a monitor display, in addition to facilitating a lay persons basic information understanding. The possible display combinations are not limited to the examples shown, rather individual examples are shown as examples of the systems flexibility.

While specific embodiments of this invention have been disclosed, it is expected that those skilled in the art can and will design alternate embodiments of this invention that fall within the scope of the accompanying claims.

We claim:

1. A patient monitoring device for producing a display from monitored data having at least two data types, the display having color and graphic display characteristics, the device comprising:

means for reading at least two data types from monitored data acquired from at least one monitoring apparatus;

means for encoding a data value from each data type into signals capable of being displayed on a display as both a color display representation and a graphic display representation, wherein the data values are represented in the color display representation by varying an attribute of at least one color and each change in data value that is displayed as a graphic display representation is also displayed on the display as a change in the color display representation substantially concurrently with the graphic display representation; and means for integrating the encoded data values for displaying actual data values on the display as a combination of the color display representation and a graphic display representation such that the data values are user comprehensible.

2. The patient monitoring device of claim 1 further comprising:

means, responsive to the means for reading, for storing the monitored data in a memory to form a sequence of stored data, wherein data read last is stored last as a present value; and wherein the means for integrating the encoded data values for displaying actual data values further integrates a sequence of stored data from the memory following encoding by the means for encoding to display a historical representation of the data values.

3. The patient monitoring device of claim 2 further comprising a user input device to enable the display to be refreshed independent of the means for reading.

4. The patient monitoring device of claim 2 further comprising:

processing means, responsive to an absence of the monitored data, for generating a sensory stimulus to notify a user of an absence of data.

5. The patient monitoring device of claim 4 wherein the absence of monitored data is due to a lack of available monitored data from the monitoring apparatus.

6. The patient monitoring device of claim 4 wherein the absence of monitored data is due to an anomaly detected in the monitored data.

7. The patient monitoring device of claim 4 further comprising:

means, responsive to the absence of monitored data, for generating at least one estimated data value from the stored monitored data.

8. The patient monitoring device of claim 1 further comprising:

means for displaying an operational range indicator to represent a range of potential data values on the display.

9. The patient monitoring device of claim 2 further comprising:

means, responsive to a user provided input, for recalling any displayed data value from the historical representation of the data values currently on display.

10. The patient monitoring device of claim 1 wherein the means for encoding a data value from each data type further encodes a single data value into a signal capable of being displayed as a color display representation and into a signal capable of being displayed as a graphic display representation, and the means for integrating integrates the encoded signals to display the representations in superimposition.

11. The patient monitoring device of claim 1 wherein the image is a superimposed image of the color display representation and the graphic display representation.

12. The patient monitoring device of claim 2 wherein the display of the historical representation of the data values is displayed as a multidimensional color and graphic image having at least a two-dimensional appearance.

13. The patient monitoring device of claim 2 wherein the display of the historical representation of the data values is displayed as a multidimensional color and graphic image having a three-dimensional appearance.

14. The patient monitoring device of claim 2 further comprising a means for selectively retrieving a stored monitored value from a memory location in the memory.

15. A method for producing a display from monitored data having at least two data types, the display having color and graphic display characteristics, the method comprising the steps of:

reading at least two data types from monitored data acquired from at least one monitoring apparatus;

encoding a data value from each data type into signals capable of being displayed on a display as both a color display representation and a graphic display representation in which actual data values are represented by varying the graphic display representation along with a corresponding change in at least one color attribute in the color display representation; and integrating the encoded data values for displaying a combination of the graphic display representation and the color display representation substantially simultaneously on the display, the display being an image of the encoded data values selected from the group consisting of one color display representation on another color display representation, a color display representation on a graphic display representation, a graphic display representation on a color display representation, and one graphic display representation on another graphic display representation.

16. The method of claim 15 further comprising the steps of:

storing the monitored data to form a sequence of stored data, wherein data read last is stored last as a present value; and wherein the step of integrating the encoded data values for displaying a combination of the graphic display representation and the color design representation substantially simultaneously further integrates a sequence of stored data following encoding by the means for encoding to display a historical representation of the data values.

17. The method of claim 16 further comprising the step of: refreshing the display independent of the step of reading.

18. The method of claim 16 further comprising the step of: generating a sensory stimulus to notify a user of an absence of the monitored data.

19. The method of claim 18 further comprising the step of: generating at least one estimated data value from the stored monitored data.

20. The method of claim 15 further comprising the step of: displaying an operational range indicator to represent a range of potential data values on the display.

21. The method of claim 16 further comprising the step of: recalling any displayed data from the historical representation of the data values concurrently on display.

22. The method of claim 15 wherein the step of encoding a data value from each data type further encodes a single data value into a signal capable of being displayed as a color display representation and into a signal capable of being displayed as a graphic display representation, and the step of integrating integrates the encoded signals to display the representations in superimposition.

23. The method of claim 15 wherein the image is a superimposed image of the color display representation and the graphic display representation.

24. The method of claim 16 wherein the display of the historical representation of the data values is displayed as a multidimensional color and graphic image having at least a two-dimensional appearance.

25. A patient monitoring device for producing a display from monitored data comprising:
a data acquisition and flow control capable of connection to at least one external monitor to receive monitored data having at least two data values;
at least one encoder connected to the data acquisition and flow control to receive and process the monitored data to create a signal capable of producing color imagery and a signal capable of producing graphic imagery, wherein the encoder encodes actual data values to be displayed as both color and graphic imagery such that the signals are free of any preprocessing threshold comparison, and are capable of representing the monitored data by varying at least one color attribute in the color imagery; and
a display integration processor to receive and integrate the signals from the encoder and produce integrated signals having both a graphic component and a color component to display an integrated indicia representation of the data values on a display device wherein the data values displayed are actual data values and the integrated indicia representation represents the actual data values simultaneously in both color imagery and graphic imagery.

26. The patient monitoring device of claim 25 wherein the integrated indicia representation is a superimposition of color imagery and graphic imagery, each representing a single value from the two data values of the monitored data.

27. The patient monitoring device of claim 25 wherein the integrated indicia representation is a superimposition of color imagery and graphic imagery, each representing a value acquired from the two data values from the monitored data.

28. The patient monitoring device of claim 25 wherein the integrated indicia representation is a multidimensional graphic representation of data values and a multicolor representation of data values.

29. The patient monitoring device of claim 28 wherein each reception of monitored data by the data acquisition and flow control updates the dimensional representation of data values and the color representation of data values with a current value acquired from the external monitors.

30. The patient monitoring device of claim 25 further comprising a data storage device connected to the data acquisition and flow control to receive monitored data and store the data in a plurality of data files, each data file corresponding to received monitor data from an external monitor.

31. The patient monitoring device of claim 30 wherein the data files contain a series of monitored data values and is capable of retrieving the series of monitored data values from the memory and encoding each data value to display a history of data values simultaneously.

32. The patient monitoring device of claim 31 wherein the historical display of data values includes a current data value as received from the external monitor, and wherein the current data value is displayed numerically.

33. The patient monitoring device of claim 31 wherein the historical display of data values is represented graphically as multiple overlapping cards arranged from an oldest value to a current value such that the current value is displayed as a top card.

34. The patient monitoring device of claim 25 wherein the data acquisition and flow control is connected to multiple external monitors, each monitor producing a different data type, and a representation of data value magnitude for each data type is displayed by adjusting a respective color, color intensity, and graphical dimensional representation of the data value as compared to a previous data value, and a current value of the data is represented numerically.

35. The patient monitoring device of claim 25 wherein the integrated indicia representation of data values includes a waveform display representation, and a current value of the data is represented numerically.

36. A patient monitoring device for producing a display from monitored data having at least two data types, the display having color and graphic display characteristics, the device comprising:
means for reading at least two data types from monitored data acquired from at least one monitoring apparatus;
means for encoding a data value from each data type into signals capable of being directly displayed as a color display representation and a graphic display representation on a same display such that a user comprehends the data values in two different representations at a same time without threshold level preprocessing;
means for integrating the encoded data values for displaying actual data values on the display as a combination of the color display representation and a graphic display representation such that the data values are user comprehensible;
means, responsive to the means for reading, for storing the monitored data in a memory to form a sequence of stored data, wherein data read last is stored last as a present value; and
wherein the means for integrating the encoded data values for displaying same further integrates a sequence of stored data from the memory following encoding by the means for encoding to display a historical representation of the data values.

37. A method for producing a display from monitored data having at least two data types, the display having color and graphic display characteristics, the method comprising the steps of:

reading at least two data types from monitored data acquired from at least one monitoring apparatus;

encoding a data value from each data type into signals that are not dependent on a predetermined threshold value, but actually represent actual data values capable of being displayed as both a color display representation and a graphic display representation substantially concurrently;

integrating the encoded data values for displaying actual data values on the display, the display being an image of the encoded data values selected from the group consisting of one color display representation on another color display representation, a color display representation on a graphic display representation, a graphic display representation on a color display representation, and one graphic display representation on another graphic display representation;

storing the monitored data to form a sequence of stored data, wherein data read last is stored last as a present value; and wherein the step of integrating the encoded data values for displaying actual data values further integrates a sequence of stored data following encoding by the means for encoding to display a historical representation of the data values.

38. A patient monitoring device for producing a display from monitored data comprising:

a data acquisition and flow control capable of connection to at least one external monitor to receive monitored data having at least two data values;

at least one encoder connected to the data acquisition and flow control to receive and process the monitored data to create a signal that is not dependent on a predetermined threshold value, but represents an actual data value and is capable of producing color imagery and a signal capable of producing graphic imagery substantially simultaneously on a display;

a display integration processor to receive and integrate the signals from the encoder and produce integrated signals having a graphic component and a color component for displaying an integrated indicia representation of the actual data values on a display device;

a data storage device connected to the data acquisition and flow control to receive monitored data and store the data in a plurality of data files, each data file corresponding to received monitor data from an external monitor; and wherein the data files contain a series of monitored data values and is capable of retrieving the series of monitored data values from the memory and encoding each data value to display a history of data values simultaneously.

39. A patient monitoring device for producing a display from monitored data comprising:

a data acquisition and flow control capable of connection to at least one external monitor to receive monitored data having at least two data values;

at least one encoder connected to the data acquisition and flow control to receive and process the monitored data to create a signal capable of producing color imagery and a signal capable of producing graphic imagery without the use of a predetermined threshold value such that actual data values can be displayed;

a display integration processor to receive and integrate the signals from the encoder and produce integrated signals having a graphic component and a color component for displaying an integrated indicia representation of the data values on a display device such that both graphic and color components are displayed to a user substantially concurrently; and wherein the data acquisition and flow control is connected to multiple external monitors, each monitor producing a different data type, and a representation of data value magnitude for each data type is displayed by adjusting a respective color, color intensity, and graphical dimensional representation of the data value as compared to a previous data value, and a current value of the data is represented numerically.

* * * * *